United States Patent [19]

Oine et al.

[11] Patent Number: 4,784,995

[45] Date of Patent: Nov. 15, 1988

[54] CEPHALOSPORIN COMPOUNDS

[75] Inventors: Toyonari Oine, Nara; Mitsuyoshi Wagatsuma; Totaro Yamaguchi, both of Urawa, all of Japan

[73] Assignee: Tanabe Seiyaku Co., Ltd., Osaka, Japan

[21] Appl. No.: 59,584

[22] Filed: Jun. 8, 1987

[30] Foreign Application Priority Data

Jun. 16, 1986 [JP] Japan .................................. 61-140988
Dec. 3, 1986 [JP] Japan .................................. 61-288080

[51] Int. Cl.$^4$ .................. C07D 501/44; A61K 31/545
[52] U.S. Cl. ..................................... 514/206; 540/225; 540/226
[58] Field of Search ................. 540/225, 226; 514/206

[56] References Cited

U.S. PATENT DOCUMENTS

| | | | |
|---|---|---|---|
| 4,258,041 | 3/1981 | O'Callaghan et al. | 424/246 |
| 4,598,075 | 7/1986 | Oine et al. | 514/203 |
| 4,598,154 | 7/1986 | Oine et al. | 548/194 |

FOREIGN PATENT DOCUMENTS

| | | |
|---|---|---|
| 0101265 | 2/1984 | European Pat. Off. . |
| 60-226884 | 11/1985 | Japan . |
| 61-78792 | 4/1986 | Japan . |

Primary Examiner—Nicholas S. Rizzo
Attorney, Agent, or Firm—Birch, Stewart, Kolasch & Birch

[57] ABSTRACT

A cephalosporin compound of the formula:

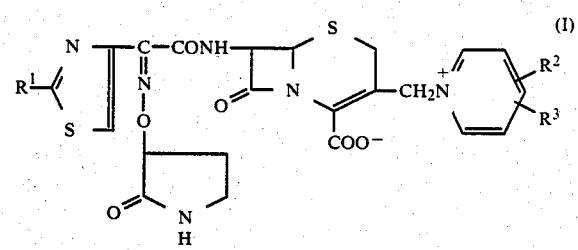

wherein
  $R^1$ is a protected or unprotected amino group;
  either one of $R^2$ and $R^3$ is a substituted or unsubstituted lower alkylthio group; sulfamoyl group; a lower alkylsulfonyl group; sulfo group; a substituted or unsubstituted amino group; a lower alkyl group; a lower alkyl group having a substituent selected from a lower alkylthio group, amino group and an acylamino group; a halogen atom; carboxy group or a lower alkoxy group; and
  the other one of $R^2$ and $R^3$ is hydrogen atom; carbamoyl group; a substituted or unsubstituted amino group; a lower alkyl group or a hydroxy-lower alkyl group; or
  $R^2$ and $R^3$ are combined together to form a lower alkylene group;

or a salt thereof and processes for preparing the same are disclosed. The cephalosporin compound (I) is useful as an antimicrobial agent.

7 Claims, No Drawings

CEPHALOSPORIN COMPOUNDS

This invnetion relates to a novel cephalosporin compound of the following formula:

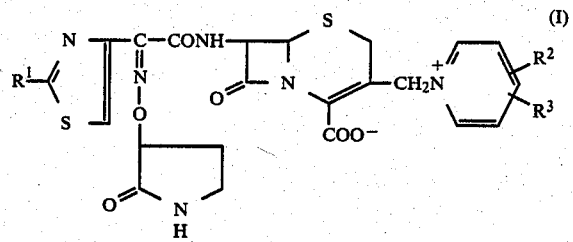

wherein
$R^1$ is a protected or unprotected amino group;
either one of $R^2$ and $R^3$ is a substituted or unsubstituted lower alkylthio group; sulfamoyl group; a lower alkylsulfonyl group; sulfo group; a substituted or unsubstituted amino group; a lower alkyl group; a lower alkyl group having a substituent selected from a lower alkylthio group, amino group and an acylamino group; a halogen atom; carboxy group or a lower alkoxy group; and
the other one of $R^2$ and $R^3$ is hydrogen atom; carbamoyl group; a substituted or unsubstituted amino group; a lower alkyl group or a hydroxy-lower alkyl group; or
$R^2$ and $R^3$ are combined together to form a lower alkylene group; or a salt thereof. It also relates to processes for preparing the same.

Many cephalosporin compounds have been known as antibacterial agents. For example, European patent publication No. 101,265 discloses 7β-{2-(2-aminothiazol-4-yl)acetamido}cephalosporin compounds such as 7β-{2-(2-aminothiazol-4-yl)-2-[(2-oxopyrrolidin-3-yl)oxyimino]acetamido}-3-[(1-pyridinio)methyl]-3-cephem-4-carboxylate and the corresponding 3-[(3- or 4-hydroxymethyl-1-pyridinio)methyl]- and 3-[(4-carbamoyl-1-pyridinio)methyl]-derivatives thereof.

We have now found that, as compared with those disclosed in said European patent publication, new cephalosporin compound (I) of the present invention and salts thereof show stronger antimicrobial activity against a wide variety of microorganisms including gram-positive and gram-negative bacteria and more useful as antibacterial agents. Thus, the compound (I) and salts thereof can be used as therapeutic agents in the treatment of a variety of infectious diseases caused by said gram-positive and gram-negative bacteria, as chemotherapeutic agents in warm-blooded animals including human being, or as supplements in animal food.

The examples of the compound of the present invention include those of the formula (I) in which $R^1$ is a protected or unprotected amino group; either one of $R^2$ and $R^3$ is a lower alkylthio group such as methylthio, ethylthio, propylthio or butylthio (said lower alkylthio group may have a substituent selected from hydroxy group, an acylamino group such as formylamino and carboxy group); sulfamoyl group; a lower alkylsulfonyl group such as methylsulfonyl, ethylsulfonyl, propylsulfonyl or butylsulfonyl; sulfo group; amino group; a lower alkyl group such as methyl, ethyl, propyl or butyl (said lower alkyl group may have a substituent selected from a lower alkylthio group such as methylthio, ethylthio, propylthio or butylthio, amino group and an acylamino group such as formylamino); a halogen atom such as chlorine, bromine, fluorine or iodine; carboxy group; or a lower alkoxy group such as methoxy, ethoxy, propoxy or butoxy; and the other one of $R^2$ and $R^3$ is hydrogen atom; carbamoyl group; amino group; a lower alkyl group such as methyl, ethyl, propyl or butyl; or a hydroxy-lower alkyl group such as hydroxymethyl, hydroxyethyl, hydroxypropyl or hydroxybutyl; or $R^2$ and $R^3$ are combined together to form a lower alkylene group such as trimethylene or tetramethylene. When $R^2$ and/or $R^3$ in the above-mentioned compound is/or are amino group(s), said amino group(s) may have 1 or 2 substituents selected from the group consisting of formyl group, a lower alkanoyl group (e.g., acetyl, propionyl or butyryl), a hydroxy-lower alkanoyl group (e.g., hydroxyacetyl, hydroxypropionyl, hydroxybutyryl), carbamoyl group, a lower alkylsulfonyl group (e.g., methylsulfonyl, ethylsulfonyl, propylsulfonyl or butylsulfonyl) and a lower alkyl group (e.g., methyl, ethyl, propyl or butyl).

Among them, a preferred subgenus includes those of the formula (I) in which $R^1$ is a protected or unprotected amino group, either one of $R^2$ and $R^3$ is a lower alkylthio group, a hydroxy-lower alkylthio group, a formylamino-lower alkylthio group, a carboxy-lower alkylthio group, sulfamoyl group, a lower alkylsulfonyl group, sulfo group, amino group, formylamino group, carbamoylamino group, a lower alkanoylamino group, a N,N-di(lower alkyl)amino group, a N-formyl-N-lower alkylamino group, a lower alkylamino group, a N-(lower alkylsulfonyl)amino group, a hydroxy-lower alkanoylamino group, a halogen atom, a lower alkoxy group, carboxy group, a formylamino-lower alkyl group, an amino-lower alkyl group, a lower alkylthio-lower alkyl group or a lower alkyl group; and the other one of $R^2$ and $R^3$ is hydrogen atom, carbamoyl group, amino group, formylamino group, a hydroxy-lower alkyl group or a lower alkyl group, or $R^2$ and $R^3$ are located at the 2- and 3-position of the pyridine ring and combined together to form a alkylene group of 3 or 4 cabon atoms.

More preferred subgenus includes those of the formula (I) in which $R^1$ is amino group, either one of $R^2$ and $R^3$ is a lower alkylthio group, a lower alkoxy group, a lower alkyl group, amino group or a halogen atom, and the other one of $R^2$ and $R^3$ is hydrogen atom or amino group.

Further preferred subgenus include those of the formula (I) in which $R^1$ is amino group, either one of $R^2$ and $R^3$ is methylthio, methoxy, methyl or amino group or bromine atom, and the other one of $R^2$ and $R^3$ is amino group.

Still further preferred subgenus includes those of the formula (I) in which $R^1$ is amino group, either one of $R^2$ and $R^3$ is methoxy or methyl group, and the other one of $R^2$ and $R^3$ is amino group.

In the compound (I) of the present invention, $R^1$ may be either amino group or a protected amino group. Examples of said protected amino group include amino group which is protected with a group selected from formyl group; a lower alkanoyl group such as acetyl or pivaloyl; a mono-, di- or trihalogeno-lower alkanoyl group such as chloroacetyl or trifluoroacetyl; a lower alkoxycarbonyl group such as methoxycarbonyl, ethoxycarbonyl or tert.-butoxycarbonyl; a substituted or unsubstituted benzyloxycarbonyl group such as benzyloxycarbonyl or p-methoxybenzyloxycarbonyl; a substituted or unsubstituted phenyl-lower alkyl group such as benzyl, p-methoxybenzyl or 3,4-dimethoxybenzyl; and a di- or triphenyl-lower alkyl group such as benzhydryl or trityl.

In the present invention, unless otherwise defined, a partial structure of the formula:

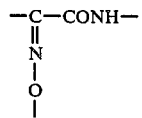

shows either one or both of the geometrical isomers of the formulas:

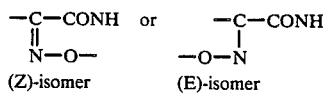

The compound (I) having (Z) (i.e. syn)-configuration in the oxyimino group is preferred for use as a medicine because of its potent biological properties, but said (Z)-isomer may include a small amount of the (E) (i.e., anti)-isomer.

The compound (I) of the present invention or a salt thereof can be prepared by the step(s) of:

(A) condensing an oxyiminoacetic acid compound of the formula:

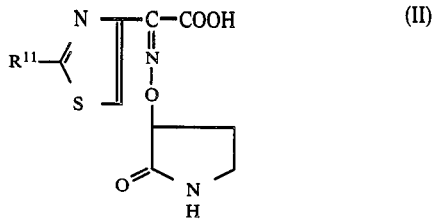

wherein R¹¹ is a protected or unprotected amino group, or a salt or reactive derivative thereof with a 7-aminocephalosporin compound of the formula:

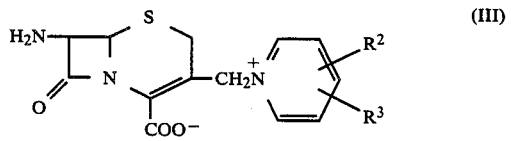

wherein R² and R³ are the same as defined above, or a salt thereof; or (B) condensing cephalosporin compound of the formula:

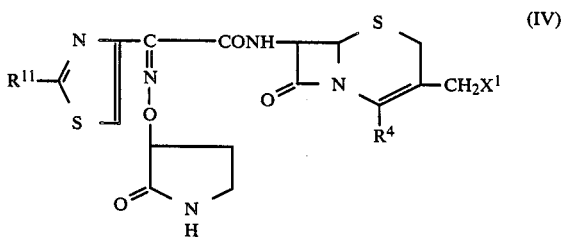

wherein R¹¹ is the same as defined above, R⁴ is a carboxy group or a protected carboxy group and X¹ is a reactive residue, or a salt thereof with a pyridine compound of the formula:

wherein R² and R³ are the same as defined above, or a salt thereof, (C)
(a) when R⁴ is protected carboxy group, removing the carboxy-protecting group, and/or
(b) when R¹¹ is a protected amino group, optionally removing the amino-protecting group, and (D) optionally converting the product into a salt thereof.

Suitable salts of the starting compounds (II) and (IV) of the present invention include, for example, inorganic salts such as sodium salt or potassium salt, or salts with organic amine such as trimethylamine salt or triethylamine salt. On the other hand, suitable salts of the starting compounds (III) and (V) include, for example, mineral acid salts such as hydrochloride, hydrobromide, hydroiodide or sulfate. When R¹¹ in the compounds (II) and (IV) is a protected amino group, a variety of amino-protecting groups which are generally used in the field of peptide synthesis can be employed as the protecting group for said amino group. For example, such protecting groups as those explained for R¹ can be used for this purpose. When R⁴ in the compound (IV) is a protected carboxy group, the carboxy-protecting group should be the one which can be easily removed by a conventional manner such as hydrolysis, acid treatment or reduction. Examples of such protecting group include a lower alkyl group such a methyl, ethyl or tert.-butyl; a substituted or unsubstituted phenyl-lower alkyl group such as benzyl, p-methoxybenzyl or p-nitrobenzyl; a benzhydryl group; a tri-lower alkylsilyl group such as trimethylsilyl, and the like. When R⁴ is carboxy group, the compound (IV) to be used for the condensation reaction should preferably be in the form of a salt thereof.

The condensation reaction of the oxyiminoacetic acid compound (II) or a salt or reactive derivative thereof with the 7-aminocephalosporin compound (III) or a salt thereof can easily be conducted in a conventional manner. For example, the condensation reaction of the oxyiminoacetic acid compound (II) in its free form or a salt thereof with the 7-aminocephalosporin compound (III) can be conducted in the presence of a dehydrating agent in a solvent. Suitable examples of the dehydrating agent include dicyclohexylcarbodiimide, N-ethyl-N'-(3-dimethylaminopropyl)carbodiimide, phosphorus oxychloride, phosphorus trichloride, thionyl chloride, oxalyl chloride, triphenyl phosphine and the like. Vilsmeier reagent prepared from dimethylformamide and phosphorus oxychloride, oxalyl chloride, phosgen or thionyl chloride may also be used as the dehydrating agent. Dioxane, tetrahydrofuran, acetonitrile, chloroform, methylene chloride, dimethylformamide, N,N-dimethylacetamide, ethyl acetate, pyridine, ethanol and water are suitable as the solvent. It is preferred to carry out the reaction at a temperature of −50° to 50° C., especially −30° to 20° C.

The condensation reaction of the reactive derivative of the oxyiminoacetic acid compound (II) with the 7-aminocephalosporin compound (III) or a salt thereof can be conducted either in the presence or absence of an acid acceptor in a solvent. Suitable examples of the reactive derivative of the oxyiminoacetic acid compound (II) include the corresponding acid halides (e.g., acid chloride, acid bromide), anhydride, mixed anhydrides (e.g., a mixed anhydride of the oxyiminoacetic acid compound (II) with an alkyl carbonate), active esters (e.g., p-nitrophenyl ester, 2,4-dinitrophenyl ester, succinimide ester, phthalimide ester, benzotriazole ester, 2-pyrrolidon-1-yl ester), acid azide and acid amides (e.g., imidazole amide, 4-substituted-imidazole amide, triazole amide). Dioxane, tetrahydrofuran, acetonitrile, chloroform, methylene chloride, dimethylformamide, N,N-dimethylacetamide, ethyl acetate, pyridine, acetone, ethanol, isopropanol and water are suitable as the solvent. Moreover, suitable examples of the acid acceptor include alkali metal hydroxides (e.g., sodium hydroxide, potassium hydroxide), alkali metal carbonates (e.g., sodium carbonate, potassium carbonate), alkali metal bicarbonate (e.g., sodium bicarbonate, potassium bicarbonate), trialkyl amines (e.g., trimethylamine, triethylamine), N,N-dialkylanilines (e.g., N,N-dimethylaniline, N,N-diethylaniline), pyridine and N-alkylmorpholines (e.g., N-methylmorpholine). It is preferred to carry out the reaction at a temperature of $-50°$ to $50°$ C., especially at $-30°$ to $20°$ C.

The condensation reaction of the cephalosporin compound (IV) or a salt thereof with the pyridine compound (V) or a salt thereof is preferably conducted in a solvent. Examples of the cephalosporin compound (IV) include the compound (IV) in which the reactive residue $X^1$ is, for example, an acyloxy group such as carbamoyloxy group, a lower alkanoyl-oxy group such as acetyloxy or propionyloxy; and a halogen atom such as bromide, chlorine or iodine. Examples of the solvent include water, heavy water or a water-miscible organic solvent which is inert to the starting materials. Such organic solvent includes, for example, dimethylformamide, dimethylacetamide, dioxane, acetone, ethanol, propanol, acetonitrile, dimethylsulfoxide, tetrahydrofuran, and the like. It is preferred to carry out the reaction at a temperature of $0°$ to $100°$ C. It is also preferred to carry out the reaction at a pH of 2 to 8, especially 5 to 8. If required, the reaction may be carried out by adding to the reaction system an alkali metal halide such as sodium iodide or potassium iodide; potassium thiocyanate; sodium bicarbonate; a surface-active quarternary ammonium salt such as trimethylbenzylammonium bromide, triethylbenzylammonium bromide, triethylbenzylammonium hydroxide; a phosphate buffer solution, and the like.

When $R^{11}$ of the thus-obtained compounds is a protected amino group and/or $R^4$ is a protected carboxy group, said protecting group or groups may be removed in conventional manners such a hydrolysis, solvolysis, acid treatment or reduction. For example, when the amino-protecting group is formyl, acetyl, tert.-butoxycarbonyl, trityl or benzhydryl and/or the carboxy-protecting group is tert.-butyl or benzhydryl, said group or groups may be removed by treating the compound with an acid such as trifluoroacetic acid, benzensulfonic acid, p-toluenesulfonic acid, formic acid, hydrochloric acid or hydrobromic acid. When the amino-protecting group is benzyloxycarbonyl, p-methoxybenzyloxycarbonyl, benzyl, p-methoxybenzyl or 3,4-dimethoxybenzyl and/or the carboxy-protecting group is benzyl, p-methoxybenzyl or p-nitrobenzyl, the removal of said protecting group or groups may be conducted by catalytic reduction in the presence of a catalyst such as a palladium-barium carbonate, palladium-carbon or palladium black in hydrogen gas. When the amino-protecting group is trifluoroacetyl, pivaloyl, methoxycarbonyl or ethoxycarbonyl and/or the carboxyl-protecting group is methyl or ethyl, said group or groups may be removed by hydrolysis with an alkali agent (e.g., sodium hydroxide, postassium hydroxide) or an acid (e.g., hydrochloric acid, hydrobromic acid). Moreover, when the amino-protecting group is chloroacetyl, said group may be removed by treating with thiourea.

Further, when $R^2$ and/or $R^3$ of the compound (I) thus obtained is/or are acylamino group(s), said acyl group(s) may be, if required, removed to give the compound (I) in which $R^2$ and/or $R^3$ are amino group(s). For example, when the acyl group is formyl, the removal of said group can be carried out by treatment with an acid (e.g., hydrochloric acid, formic acid, hydrobromic acid, trifluoroacetic acid). It is preferred to carry out the reaction at a temperature between room temperature and $80°$ C., especially at a temperature of $30°$ to $60°$ C.

A salt of the compound (I) can be readily obtained in a conventional manner, for example, by treating it with a substantially equimolar amount of an alkali agent or an acid in an aqueous solvent at room temperature.

The compound (I) of the present invention and salts thereof show potent antimicrobial activity against gram-positive and gram-negative bacteria including a wide variety of microorganisms belonging to the genera Staphylococcus, Escherichia, Salmonella, Klebsiella, Proteus, Citrobacter, Enterobacter and Serratia. The compound (I) and salts thereof also show potent antimicrobial activity against bacteria belonging to the genera Pseudomonas, Shigella and Enterococcus. For example, when the minimum inhibitory concentration (M.I,C.) of a test compound was examined by means of the standard agar plate dilution method (based on the standard method of Japan Society of Chemotherapy) using media of Muller-Hinton agar (MHA; Nissui), the anti-microbial activity of 7β-{(Z)-2-(2-aminothiazol-4-yl)-2-[((3S)-2-oxopyrrolidin-3-yl)oxyimino]acetamido}-3-[(3-amino-5-methoxy-1-pyridinio)methyl]-3-cephem-4carboxylate of the present invention against *Staphylococcus aureus* 252 R, *Proteus morganii* 6501, *Proteus rettgeri* 6259 and *Enterobacter cloacae* TU-680 were not less than about 4 times stronger as compared with those of 7β-{(Z)-2-(2-aminothiazol-4-yl)-2-[((3S)-2-oxopyrrolidin-3-yl)oxyimino]acetamido}-3-[(1-pyridinio)methyl]-3-cephem-4-carboxylate disclosed in European patent publication No. 101,265. The anti-microbial activity of said compound of the invention against *Staphylococcus aureus* Terajima, *Escherichia coli* NIHJ JC-2, *Salmonella typhimurium, Proteus vulgaris* IID-874, *Proteus inconstans* 6764, *Citrobacter freundii* TL-12 and *Serratia marcescens* 7006 were also about 2 times stronger than those of the compound of the European patent publication. Moreover, when the 50% minimum inhibitory concentration against clinically isolated strains was examined in the same manner as mentioned above, the antimicrobial activity of 7β-{(Z)-2-(2-aminothiazol-4-yl)-2-[((3S)-2-oxopyrrolidin-3-yl)oxyimino]acetamido}-3-[(3-amino-5-methoxy-1-pyridinio)methyl]-3-cephem-4-carboxylate of the present invention against *Staphylococcus*

*aureus* (methicillin-resistant bacteria, 19 strains), *Citrobacter freundii* (20 strains), *Enterobacter* sp. (20 strains), *Serratia marcescens* (20 strains) were about 2 to 4 times stronger as compared with those of the above-mentioned compound of European patent publication.

Further, the compound (I) and salts thereof are characterized in that they show potent protective effects against infectious diseases of various bacteria including Staphylococcus aureus and Pseudomonas aeruginosa. The compound (I) and salts thereof are also characterized by a potent antimicrobial activity in vivo because of their high absorbability or long-lasting therapeutic effects in living tissues. For example, each test compound was administered intramuscularly to mice which were challenged via the intraperitoneal route with bacteria sufficient to kill all non-treated mice within 24 hours, and then the 50% effective dose ($ED_{50}$) thereof was estimated 7 days after the infection by the probit method on the basis of survival ratios of mice. In this experiments, the protective effects of 7β-{(Z)-2-(2-aminothiazol-4-yl)-2[((3S)-2-oxopyrrolidin-3-yl)oxyimino)acetamido}-3-[(3-amino-5-methoxy-1-pyridinio)methyl]-3-cephem-4-carboxylate of the present invention against Staphylococcus aureus Smith (diffuse type), *Staphylococcus aureus* 712 and *Pseudomonas aeruginosa* TU-408 were respectively about 6, 2 and 3.5 times superior to those of the above-mentioned compound disclosed in European patent publication No. 101,265.

Moreover, the compound (I) and salts thereof have a high stability against a variety of β-lactamase-producting microorganisms, for example, against β-lactamases produced by *Escherichia coli* ML-1410 RGN-823 or *Proteus vulgaris* GN76/C-1. The compound (I) and salts thereof are also low in toxicity.

The compound (I) can be used for pharmaceutical use either in the free form or in the form of a salt thereof. Pharmaceutically acceptable salts of the compound (I) include, for example, non-toxic inorganic salts such as sodium salt, potassium salt, calcium salt or aluminium salt; salts with non-toxic organic amines such as trialkyl amines (e.g., triethylamine), pyridine, ethanolamine, triethanolamine, dicyclohexylamine; salts with inorganic acids such as hydrochloric acid, hydrobromic acid or sulfuric acid; salts with organic acids such as oxalic acid or tartaric acid; salts with amino acid such as glycine, lysine, arginine, aspartic acid, glutamic acid and so forth. The salts of the compound (I) also include salts with a resin such as polystyrene resin containing amino group, a quaternary ammonium group or sulfonic acid group, or a polyacrylic acid resin containing carboxy group. Moreover, they may be the complex salts with an alkali or alkaline earth metal salt such as sodium chloride, potassium chloride, sodium sulfate, calcium chloride or with an ammonium salt such as ammonium chloride. As is clear from the above, therefore, the salts of the compound (I) of the present invention should be interpreted to include all of the intramolecular salt, adduct, complex salts, solvate and hydrate thereof. The compound (I) and salts thereof can be administered either orally or parenterally (e.g., intravenously, intramuscularly, subcutaneously). The daily dose of the compound (I) or a salt thereof may vary over a wide range depending on the age, weight or conditions of patients and the severity of diseases to be treated. In general, however, a preferred daily dose of said compound (I) or a salt thereof may be about 0.002 to 0.2 g, especially 0.01 to 0.04 g, per kg of body weight per day. Further, the compound (I) and salts thereof may be used in the form of a pharmaceutical preparation containing the same compound in conjunction or admixture with pharmaceutical excipients suitable for oral or parenteral administration. Suitable excipients include, for example, gelatin, lactose, glucose, sodium chloride, starch, magnesium stearate, talcum, vegetable oil and other known medicinal excipients. The pharmaceutical preparations may be in solid form such as tablets, granules or capsules; or in liquid form such as solutions, suspensions or emulsions. They may be sterillized and/or may further contain auxiliaries such as stabilizing, wetting or emulsifying agent.

Concomitantly, the starting compound (II) of the present invention may be prepared, for example, by the method disclosed in European patent publication No. 147,181. The starting compound (III) may be prepared, for example, by reacting a 7-aminocephalosporanic acid or a salt thereof with the compound (V) in the same manner as described in the reaction of compounds (IV) and (V). On the other hand, the compound (IV) may be prepared, for example, by reacting the compound (II) with a 7-aminocephalosporin compound of the formula:

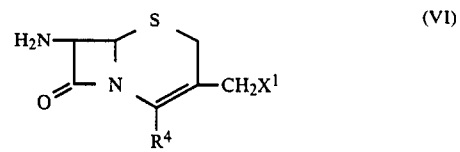

wherein $X^1$ and $R^4$ are the same as defined above, according to the method disclosed in European patent publication No. 101,265.

While the compound (I) of the invention and the starting compounds (II) and (IV) can exist in the form of optical isomers due to the asymmetric carbon atom involved in the group of the formula:

wherein the asterisk denotes an asymmetric carbon atom, the present invention includes both of such optical isomers and a racemic modification thereof.

Throughtout the specification and claims, the term "lower alkyl", "lower alkoxy", "lower alkanoyl" and "lower alkylene" should be interpreted as referring to alkyl having one to four carbon atoms, alkoxy having one to four carbon atoms, alkanoyl having two to five carbon atoms and alkylene having three to five carbon atoms, respectively.

EXAMPLE 1

(1) 2.2 g of (Z)-2-(2-tritylaminothiazol-4-yl)-2-[((3S)-2-oxopyrrolidin-3-yl)oxyimino]acetic acid dihydrate are dissolved in a mixture of 9.5 ml of dimethylacetamide and 14.5 ml of methylene chloride. The mixture is cooled to −20° C. 2.45 g of phosphorus oxychloride are added dropwise thereto with stirring at −15° to −20° C. The mixture is stirred at −5° C. for 10 minutes and then cooled to −35° C. (The resulting solution is referred to as "Solution A".).

On the other hand, 1.92 g of 7β-amino-3-[(3-amino-5-methoxy-1-pyridinio)methyl]-3-cephem-4-carboxylate hydroiodide dihydrate are suspended in 19 ml of ethanol, and 12 ml of water are added thereto with stirring. The mixture is cooled to −20° C. and 8.8 ml of triethylamine are added dropwise thereto. The mixture is stirred at −20° C. until it becomes a clear solution, and then cooled to −35° C. "Solution A" obtained above is added thereto and the mixture is stirred vigorously. The mixture is stirred at −15° to −20° C. for 10 minutes, and 20 ml of 6N-sulfuric acid are added dropwise thereto. The precipitated crystals are collected, washed with water and dried, whereby 2.7 g of 7β-{(Z)-2-(2-tritylaminothiazol-4-yl)-2-[((3S)-2-oxopyrrolidin-3-yl)oxyimino]acetamido}-3-[(3-amino-5-methoxy-1-pyridinio)methyl]-3-cephem-4-carboxylate are obtained.

(2) The product obtained above is dissolved in 20 ml of 88% formic acid and stirred at room temperature for 20 minutes. Insoluble materials are filtered off and the filtrate is evaporated to dryness under reduced pressure. Ether is added to the residue. The resulting powder is collected by filtration, dissolved in 50 ml of water and passed through a column packed with a non-ionic adsorption resin (manufactured by Mitsubishi Chemical Industries Ltd. under the trade name "Diaion CHP-20P"; hereinafter referred to as "CHP-20P"). The fractions containing the desired product are collected and evaporated to dryness under reduced pressure, whereby 1.5 g of 7β-{(Z)-2-(2-aminothiazol-4-yl)-2-[((3S)-2-oxopyrrolidin-3-yl)oxyimino]acetamido}-3-[(3-amino-5-methoxy-1-pyridinio)methyl]-3-cephem-4-carboxylate are obtained.

m.p. 180°–195° C. (decomposition).

NMR ($D_2O + CF_3COOD$)δ: 2.0–2.7(2H, m), 3.20(1H, d, J=18 Hz), 3.2–3.6(2H, m), 3.63(1H, d, J=18 Hz), 3.88(3H, s), 5.03(1H, t, J=7 Hz), 5.07(1H, d, J=14 Hz), 5.22(1H, d, J=5 Hz), 5.37(1H, d, J=14 Hz), 5.77(1H, d, J=5 Hz), 7.00(1H, s), 7.10(1H, br.s), 7.80(2H, br.s).

EXAMPLE 2

(1) A mixture of 1.8 ml of water and 5.25 g of sodium iodide is heated at 80° C., and 0.95 g of 3-formylamino-5-methoxypyridine and 1.34 g of 7β-{(Z)-2-(2-aminothiazol-4-yl)-2-[((3S)-2-oxopyrrolidin-3-yl)oxyimino]acetamido}-cephalosporanic acid are added thereto. The mixture is stirred at the same temperature for 30 minutes. After cooling, 30 ml of water are added to the mixture and insoluble materials are filtered off. The filtrate is passed through a column packed with CHP-20P. The column is washed with water and eluted with 25% aqueous methanol solution. The fractions containing the desired product are collected and evaporated to dryness under reduced pressure. Acetone is added to the residue and the resulting powder is collected by filtration and dried, whereby 360 mg of 7β-{(Z)-2-(2-aminothiazol-4-yl)-2-[((3S)-2-oxopyrrolidin-3-yl)oxyimino]acetamido}-3-[(3-formylamino-5-methoxy-1-pyridinio)methyl]-3-cephem-4-carboxylate are obtained.

m.p. 164°–175° C. (decomposition).

NMR ($D_2O$)δ: 2.1–2.6(2H, m), 3.0–3.8(4H, m), 3.90(3H, s), 4.93(1H, t, J=8 Hz), 5.13(1H, d, J=14 Hz), 5.19(1H, d, J=5 Hz), 5.50(1H, d, J=14 Hz), 5.72(1H, d, J=5 Hz), 6.72(1H, s), 7.87(1H, m) 8.27(1H, s), 8.41(1H, br.s), 8.90(1H, br.s).

(2) A mixture of 260 mg of 7β-{(Z)-2-(2-aminothiazol-4-yl)-2-[((3S)-2-oxopyrrolidin-3-yl)oxyimino]acetamido}-3-[(3-formylamino-5-methoxy-1-pyridinio)methyl]-3-cephem-4-carboxylate and 6 ml of 5% hydrochloric acid is stirred at 40° C. for 45 minutes. The mixture is cooled and adjusted to about pH 4.8 with an anion exchange resin (manufactured by Rohm & Haas Co., U.S.A. under the trade mark "Amberlite IRA-93"); hereinafter referred to as "IRA-93"). The resin is filtered off and the filtrate is passed through a column packed with CHP-20P. The column is washed with water and eluted with 30% aqueous methanol solution. The fractions containing the desired product are collected and evaporated to dryness under reduced pressure. Acetone is added to the residue. The resulting power is collected by filtration, whereby 102 mg of 7β-{(Z)-2-(2-aminothiazol-4-yl)-2-[((3S)-2-oxopyrrolidin-3-yl)oxyimino]acetamido}-3-[(3-amino-5-methoxy-1-pyridinio)methyl]-3-cephem-4-carboxylate are obtained.

The physico-chemical properties of this product are identical with those of the product obtained in Example 1–(2).

EXAMPLE 3

A mixture of 2 ml of dimethylformamide and 2 ml of water is heated at 75°–80° C., and 8 g of sodium iodide and 1.6 g of 2-methylthiopyridine are added thereto. 2.0 g of 7β-{(Z)-2-(2-tritylaminothiazol-4-yl)-2-[((3S)-2-oxopyrrolidin-3-yl)oxyimino)acetamido}cephalosporanic acid are added to the mixture, and the mixture is stirred at 80° C. for one hour. After cooling, 40 ml of water are added to the mixture, and the mixture is adjusted to pH 1 with 6N-$H_2SO_4$ under ice-cooling. The precipitates are collected by filtration and washed with water, whereby 7β-{(Z)-2-(2-tritylaminothiazol-4-yl)-2-[((3S)-2-oxopyrrolidin-3-yl)oxyimino]acetamido}-3-[(2-methylthio-1-pyridinio)methyl]-3-cephem-4-carboxylate is obtained as crude product. The crude product is dissolved in 12 ml of 88% formic acid, and the mixture is stirred at room temperature for one hour. 40 ml of water are added to the mixture, and insoluble materials are filtered off. The filtrate is washed with ether and concentrated to dryness under reduced pressure. The residue is dissolved in 40 ml of water and the solution is adjusted to pH 6.0 with an aqueous sodium bicarbonate solution. Insoluble materials are filtered off, and the filtrate is chromatographed on a column of CHP-20. The column is washed with water, followed by elution with an aqueous 25% methanol solution. The fractions containing the desired product are collected and concentrated to dryness under reduced pressure at a temperature of below 40° C. Acetone is added to the residue, and the resulting powder is collected by filtration, whereby 200 mg of 7β-{(Z)-2-(2-aminothiazol-4-yl)-2-[((3S)-2-oxopyrrolidin-3-yl)oxyimino]acetamido}-3-[(2-methylthio-1-pyridinio)methyl]-3-cephem-4-carboxylate are obtained.

$IR\nu_{Max}^{Nujol}$ (cm$^{-1}$): 1780, 1690.

NMR ($D_2O$)δ: 2.0–2.7(2H, m), 2.76(3H, s), 3.1–3.6(4H, m), 4.96(1H, t, J=7 Hz), 5.13(1H, d, J=5 Hz), 5.18(1H, d, J=15 Hz), 5.65(1H, d, J=15 Hz), 5.75(1H, d, J=5 Hz), 6.83(1H, s), 7.4–7.8(2H, m), 8.0–8.3(1H, m), 8.53(1H, d, J=7 Hz).

EXAMPLE 4

A mixture of 0.4 ml of dimethylformamide and 3.2 ml of water is heated at 75°–80° C., and 9.44 g of sodium iodide and 1.41 g of 3-methylthiopyridine are added thereto. 2.41 g of 7β-[(Z)-2-(2-aminothiazol-4-yl)-2-

[((3S)-2-oxopyrrolidin-3-yl)oxyimino)acetamido}cephalosporanic acid are added to the mixture and the mixture is stirred at 80° C. for one hour. After the reaction, the reaction mixture is concentrated to dryness under reduced pressure. 80 ml of acetone are added to the residue and the mixture is stirred. Insoluble powder is collected by filtration and washed with acetone. The powder thus obtained is added to 40 ml of water, and the mixture is adjusted to pH 6 with an aqueous sodium bicarbonate solution. Insoluble materials are filtered off, and the filtrate is chromatographed on a column of CHP-20. The column is washed with water, followed by elution with an aqueous 25% methanol solution. The fractions containing the desired product are collected and concentrated to dryness under reduced pressure, whereby 750 mg of 7β-{(Z)-2-(2-aminothiazol-4-yl)-2-[((3s)-2-oxopyrrolidin-3-yl)oxyimino]acetamido}-3-[(3-methylthio-1-pyridinio)methyl]-3-cephem-4-carboxylate are obtained as powder.

NMR (D$_2$O)δ: 2.1–2.9(2H, m), 2.64(3H, s), 3.0–3.9(4H, m), 5.03(1H, t, J=7 Hz), 5.25(1H, d, J=15 Hz), 5.28(1H, d, J=5 Hz), 5.60(1H, d, J=15 Hz), 5.82(1H, d, J=5 Hz), 6.90(1H, s), 7.7–8.0(1H, m), 8.1–8.4(1H, m), 8.5–8.7(1H, m), 8.82(1H, s).

EXAMPLE 5

(1) A mixture of 50 ml of water and 140 g of sodium iodide is heated at 75° to 80° C., and 26 g of 3-formylamino-5-methoxypyridine and 36.6 g of 7β-{(Z)-2-(2-aminothiazol-4-yl)-2-[((3S)-2-oxopyrrolidin-3-yl)oxyimino]acetamido}-cephalosporanic acid are added thereto. The mixture is stirred at 80° C. for 30 minutes. The mixture is evaporated to dryness under reduced pressure, and 1000 ml of acetone are added to the residue. The resulting powder is collected by filtration, whereby 7β-{(Z)-2-(2-aminothiazol-4-yl)-2-[((3S)-2-oxopyrrolidin-3-yl)oxyimino]acetamido}-3-[(3-formylamino-5-methoxy-1-pyridinio)methyl]-3-cephem-4-carboxylate is obtained as a crude product.

(2) The product obtained above is dissolved in 1.2 liter of 5% hydrochloric acid and insoluble materials are filtered off. The filtrate is stirred at 40° C. for one hour, and adjusted to pH about 4.5 with an aqueous sodium hydroxide solution with stirring under cooling, and then concentrated under reduced pressure to a volume of about 500 ml. The concentrated solution is passed through a column packed with CHP-20P. The column is washed with water and eluted with an aqueous 30% methanol solution. The fractions containing the desired product are collected and evaporated to dryness under reduced pressure, whereby 8.1 g of 7β-{(Z)-2-(2-aminothiazol-4-yl)-2-[((3S)-2-oxopyrrolidin-3-yl)oxyimino)acetamido}-3-[(3-amino-5-methoxy-1-pyridinio)methyl]-3-cephem-4-carboxylate are obtained.

The physico-chemical properties of this product are identical with those of the product obtained in Example 1-(2).

EXAMPLE 6

(1) A mixture of 3.6 ml of water and 10.5 g of sodium iodide is heated at 80° C., and 1.7 g of 3-formylamino-2-methylpyridine and 2.68 g of 7β-[(Z)-2-(2-aminothiazol-4-yl)-2-[((3S)-2-oxopyrrolidin-3-yl)oxyimino)acetamido}cephalosporanic acid are added thereto. The mixture is stirred at 80° to 82° C. for 30 minutes and evaporated to dryness under reduced pressure. 100 ml of acetone are added to the residue. The resulting powder is collected by filtration and dissolved in 80 ml of water. Insoluble materials are filtered off, and the filtrate is passed through a column packed with CHP-20P. The column is washed with water and eluted with 25% aqueous methanol solution. The fractions containing the desired product are collected and evaporated to dryness under reduced pressure, whereby 7β-{(Z)-2-(2-aminothiazol-4-yl)-2-[((3S)-2-oxopyrrolidin-3-yl)oxyimino]acetamido}-3-[(3-formylamino-2-methyl-1-pyridinio)methyl]-3-cephem-4-carboxylate is obtained.

(2) The product obtained above is dissolved in 10 ml of 5% hydrochloric acid and the mixture is stirred at 40° C. for 40 minutes. The mixture is adjusted to about pH 4.5 with IRA-93. The resin is filtered off and the filtrate is passed through a column packed with CHP-20P. The column is washed with water and eluted with 30% aqueous methanol solution. The fractions containing the desired product are collected and evaporated to dryness under reduced pressure. Acetone is added to the residue. The resulting powder is collected by the filtration, whereby 320 mg of 7β-{(Z)-2-(2-aminothiazol-4-yl)-2-[((3S)-2-oxopyrrolidin-3-yl)oxyimino]acetamido}-3-[(3-amino-2-methyl-1-pyridinio)methyl]-3-cephem-4-carboxylate are obtained.

m.p. 178°–185° C. (decomposition).

NMR (D$_2$O)δ: 2.0–2.7(2H, m), 2.51(3H, s), 2.9–3.6(4H, m), 4.95(1H, t, J=7 Hz), 5.13(1H, d, J=5 Hz), 5.18(1H, d, J=15 Hz), 5.52(1H, d, J=15 Hz), 5.73(1H, d, J=5 Hz), 6.81(1H, s), 7.2–7.6(2H, m), 7.90(1H, m).

EXAMPLES 7 TO 8

The corresponding starting compounds are treated in the same manner as described in Example 1-(1) to give the following compounds.

(7) 7β-{(Z)-2-(2-tritylaminothiazol-4-yl)-2-[((3S)-2-oxopyrrolidin-3-yl)oxyimino]acetamido}-3-[(2-methylthio-1-pyridinio)methyl]-3-cephem-4-carboxylate.

IRν$_{Max}$$^{Nujol}$ (cm$^{-1}$): 1775, 1675.

NMR (DMSO-d$_6$)δ: 2.1–2.5(2H, m), 3.12(3H, s), 2.7–3.4(4H, m), 4.60(1H, t, J=7 Hz), 5.00(1H, d, J=5 Hz), 5.4–5.9(3H, m), 6.60(1H, s), 7.2(15H), 7.6–8.0(1H, m), 8.1–8.4(1H, m), 8.6–8.9(2H, m), 9.3–9.6(1H, m).

(8) 7β-{(Z)-2-(2-tritylaminothiazol-4-yl)-2-[((3S)-2-oxopyrrolidin-3-yl)oxyimino]acetamido}-3-[(3-amino-1-pyridinio)methyl]-3-cephem-4-carboxylate.

m.p. 180°–195° C. (decompositon).

IRν$_{Max}$$^{Nujol}$ (cm$^{-1}$): 1780, 1695.

NMR (DMSO-d$_6$)δ: 2.1–2.4(2H, m), 2.9–3.3(4H, m), 4.8–5.3(3H, m), 5.05(1H, d, J=5 Hz), 5.5–5.7(1H, m), 6.59(1H, s), 7.16(15H, s), 7.45–7.60(1H, m), 7.75–7.8(1H, m), 7.9–8.2(2H, m).

EXAMPLE 9 TO 10

The corresponding starting compounds are treated in the same manner as described in Example 1-(2) to give the following compounds.

(9) 7β-{(Z)-2-(2-aminothiazol-4-yl)-2-[((3S)-2-oxopyrrolidin-3-yl)oxyimino]acetamido}-3-[(2-methylthio-1-pyridinio)methyl]-3-cephem-4-carboxylate The physico-chemical properties of this product are identical with those of the product obtained in Example 3.

(10) 7β-{(Z)-2-(2-aminothiazol-4-yl)-2-[((3S)-2-oxopyrrolidin-3-yl)oxyimino]acetamido}-3-[(3-amino-1-pyridinio)methyl]-3-cephem-4-carboxylate IRν$_{Max}$$^{Nujol}$ (cm$^{-1}$): 1770, 1690, 1660.

NMR (D₂O-CD₃OD+CF₃CO₂D)δ:2.2-2.7(2H, m), 3.2-3.5(2H, m), 3.21(1H, d, J=18 Hz), 3.67(1H, d, J=18 Hz), 4.95(1H, t, J=7 Hz), 5.11(1H, d, J=15 Hz), 5.21(1H, d, J=5 Hz), 5.55(1H, d, J=15 Hz), 5.82(1H, d, J=5 Hz), 6.95(1H, s), 7.5-7.6(2H, m), 7.9-8.2(2H, m).

EXAMPLE 11 TO 26

The corresponding starting compounds are treated in the same manner as described in Example 2 to give the compounds shown in Table 1.

TABLE 1

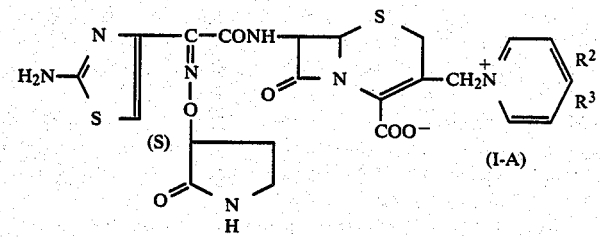

(I-A)

| EX No. | Compound (I-A) $R^2$ & $R^3$ | Properties |
|---|---|---|
| 11 | $R^2$ = 3-NHCHO<br>$R^3$ = 4-CH₃ | m.p. 162–170° C. (decomposition)<br>NMR(D₂O)δ:<br>2.0–2.75(2H,m), 2.50(3H,s), 3.0–3.85(4H,m), 4.93(1H,t,J=8Hz), 5.14(1H,d,J=15Hz), 5.18 (1H,d,J=5Hz), 5.48(1H,d,J=15Hz), 5.73(1H, d,J=5Hz), 6.78(1H,s), 7.74(1H,d,J=6Hz), 8.13(1H,s), 8.47(1H,d,J=6Hz), 9.37(1H,s) |
| 12 | $R^2$ = 3-NH₂<br>$R^3$ = 4-CH₃ | m.p. 180–190° C. (decomposition)<br>NMR(D₂O)δ:<br>2.0–2.7(2H,m), 2.29(3H,s), 2.9–3.7(4H,m), 4.97 (1H,t,J=8Hz), 4.9–5.5(2H,m), 5.19(1H,d,J=5Hz), 5.75(1H,d,J=5Hz), 6.83(1H,s), 7.43(1H,d, J=6Hz), 7.92(1H,d,J=6Hz), 8.60(1H,s) |
| 13 | $R^2$ = 3-NHCHO<br>$R^3$ = 5-SCH₃ | m.p. 168–175° C. (decomposition)<br>NMR(D₂O)δ:<br>2.1–2.7(2H,m), 2.71(3H,s), 3.2–3.9(4H,m), 5.12 (1H,t,J=8Hz), 5.25(1H,d,J=15Hz), 5.35(1H, d,J=5Hz), 5.75(1H,d,J=15Hz), 5.93(1H,d,J=5Hz), 7.10(1H,s), 8.52(1H,s), 8.72(1H,br,s), 9.05–9.25(2H,m) |
| 14 | $R^2$ = 3-NH₂<br>$R^3$ = 5-SCH₃ | m.p. 180–190° C. (decomposition)<br>NMR(D₂O—CF₃CO₂D)δ:<br>2.1–2.7(2H,m), 2.56(3H,s), 3.35(1H,d,J=18Hz), 3.3–3.7(2H,m), 3.75(1H,d,J=18Hz), 5.13 (1H,t,J=9Hz), 5.20(1H,d,J=15Hz), 5.32(1H,d, J=5Hz), 5.62(1H,d,J=15Hz), 5.88(1H,d,J=5Hz), 7.16(1H,s), 7.45(1H,s), 7.96(2H,br,s), |
| 15 | $R^2$ = 3-NHCHO<br>$R^3$ = 5-Br | m.p. 160–170° C. (decomposition)<br>NMR(D₂O—CD₃CN)δ:<br>2.3–2.9(2H,m), 3.45(1H,d,J=17Hz), 3.4–3.8(2H, m), 3.90(1H,d,J=17Hz), 5.23(1H,t,J=7Hz), 5.45 1H,d,J=14Hz), 5.49(1H,d,J=5Hz), 5.92(1H,d,J= 14Hz), 6.08(1H,d,J=5Hz), 7.19(1H,s), 8.71(1H, s), 9.50(1H,d,J=2Hz), 9.30(1H,d,J=2Hz), 9.73 (1H,d,J=2Hz) |
| 16 | $R^2$ = 3-NH₂<br>$R^3$ = 5-Br | m.p. 177–185° C. (decomposition)<br>NMR(D₂O—CF₃CO₂D)δ:<br>2.1–2.9(2H,m), 3.38(1H,d,J=18Hz), 3.4-3.7(2H,m), 3.80(1H,d,J=18Hz), 5.16(1H,t,J=9Hz), 5.25(1H,d, J=15Hz), 5.36(1H,d,J=5Hz), 5.70(1H,d,J=15Hz), 5.92(1H,d,J=5Hz), 7.20(1H,s), 7.90(1H,d,J=2Hz), 8.2–8.4(2H,m) |
| 17 | $R^2$ = 3-NHCHO<br>$R^3$ = 4-SCH₃ | m.p. 170–190° C. (decomposition)<br>NMR(D₂O+CD₃CN)δ:<br>2.1–2.7(2H,m), 2.75(3H,s), 3.17(1H,d,J=18Hz), 3,72(1H,d,J=18Hz), 3.2–3.7(2H,m), 5.00(1H,t, J=7Hz), 5.10(1H,d,J=15Hz), 5.25(1H,d,J=5Hz), 5.48(1H,d,J=15Hz), 5.81(1H,d,J=5Hz), 6.90(1H, s), 7.74(1H,d,J=8Hz), 8.40(1H,s), 8.55(1H,d,J=8Hz), 9.10(1H,s) |
| 18 | $R^2$ = 3-NH₂<br>$R^3$ = 4-SCH₃ | m.p. 185–200° C. (decomposition)<br>NMR(D₂O+CD₃CN)δ:<br>2.3–2.8(2H,m), 2.95(3H,s), 3.4–3.8(2H,m), 3.35 (1H,d,J=15Hz), 3.83(1H,d,J=15Hz), 5.18(1H,d, J=15Hz), 5.22(1H,t,J=7Hz), 5.25(1H,d,J=15Hz), 5.45(1H,d,J=5Hz), 6.02(1H,d,J=5Hz), 6.95(1H,s), 7.68(1H,d,J=5Hz), 8.28(1H,s), 8.28(1H,d,J=5Hz) |
| 19 | $R^2$ = 3-NHCHO<br>$R^3$ = H | IRν$_{Max}^{KBr}$ (cm⁻¹): 1770, 1690, 1610<br>NMR(D₂O)δ:<br>2.1–2.8(2H,m), 3.15–3.85(4H,m), 5.03(1H,t,J=7Hz), 5.1–5.8(2H,m), 5.30(1H,d,J=5Hz), 5.86(1H,d, J=5Hz), 6.93(1H,s), 7.9–8.1(1H,m), 8.3–8.5(1H,m) |

TABLE 1-continued

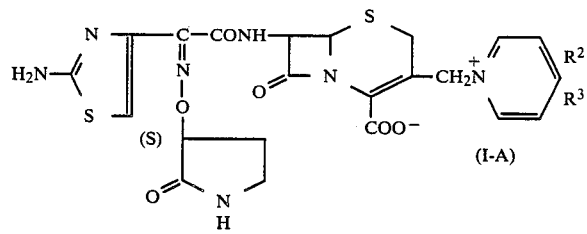

(I-A)

| EX No. | Compound (I-A) $R^2$ & $R^3$ | Properties |
|---|---|---|
| 20 | $R^2$ = 3-$NH_2$<br>$R^3$ = H | 8.40(1H,m), 8.65-8.75(1H,m), 9.4-9.5(1H,br.s)<br>IR$\nu_{Max}^{Nujol}$ (cm$^{-1}$): 1770, 1690, 1660<br>NMR($D_2O-CD_3OD+CF_3CO_2D$)δ:<br>2.2-2.7(2H,m), 3.2-3.5(2H,m), 3.21(1H,d,J=18Hz),<br>3.67(1H,d,J=18Hz), 4.95(1H,t,J=7Hz), 5.11(1H,d,<br>J=15Hz), 5.21(1H,d,J=5Hz), 5.55(1H,d,J=15Hz),<br>5.82(1H,d,J=5Hz), 6.95(1H,s), 7.5-7.6(2H,m),<br>7.9-8.2(2H,m) |
| 21 | $R^2$ = 2-$CH_3$<br>$R^3$ = 5-$NH_2$ | m.p. 170-178° C. (decomposition)<br>NMR($D_2O$)δ:<br>2.0-2.85(2H,m), 2.61(3H,s), 3.0-3.7(4H,m), 5.03<br>(1H,t,J=6Hz), 5.15(1H,d,J=15Hz), 5.25(1H,d,<br>J=5Hz), 5.45(1H,d,J=15Hz), 5.84(1H,d,J=5Hz),<br>6.93(1H,s), 7.4-7.7(2H,m), 8.08(1H,m) |
| 22 | $R^2$ = 3-$NH_2$<br>$R^3$ = 5-$NH_2$ | m.p. The product begins to gradually decompose<br>at 175° C.<br>NMR($D_2O+CD_3CN$)δ:<br>2.1-2.6(2H,m), 3.02(1H,d,J=18Hz), 3.47(1H,d,<br>J=18Hz), 3.1-3.5(2H,m), 4.81(1H,d,J=14Hz), 4.88<br>(1H,t,J=7Hz), 5.09(1H,d,J=5Hz), 5.12(1H,d,<br>J=14Hz), 5.67(1H,d,J=5Hz), 6.81(1H,s,), 6.67<br>(1H,t,J=2Hz), 7.40(2H,d,J=2Hz) |
| 23 | $R^2$ = 3-$NH_2$<br>$R^3$ = 5-COOH | m.p. 160-165° C. (decomposition)<br>IR$\nu_{Max}^{KBr}$ (cm$^{-1}$): 1760, 1690, 1580-1640<br>NMR ($D_2O+CD_3CN+CF_3CO_2D$)δ:<br>2.20-2.80(2H,m), 3.20-3.60(2H,m), 3.30(1H,d,<br>J=18Hz), 3.70(1H,d,J=18Hz), 5.07(1H,t,J=9Hz),<br>5.23(1H,d,J=15Hz), 5.29(1H,d,J=5Hz), 5.70(1H,<br>d,J=15Hz), 5.89(1H,d,J=5Hz), 7.13(1H,s), 8.18<br>(br.s,1H), 8.37(br.s,1H), 8.61(br.s,1H) |
| 24 | $R^2$ = 3-$NH_2$<br>$R^3$ = 5-$CH_2OH$ | m.p. 170-175° C. (decomposition)<br>IR$\nu_{Max}^{KBr}$ (cm$^{-1}$):1770, 1690<br>NMR ($D_2O+CF_3CO_2D$)δ:<br>2.20-2.75(2H,m), 3.35-3.68(2H,m), 3.30(1H,d,<br>J=18Hz), 3.75(1H,d,J=18Hz), 4.78(2H,s),<br>5.15(1H,t,J=8Hz), 5.23(1H,d,J=15Hz), 5.36(1H,<br>d,J=5Hz), 5.68(1H,d,J=15Hz), 5.92(1H,d,J=5Hz),<br>7.21(1H,s), 7.65-7.75(1H,m), 8.10-8.20(2H,m) |
| 25 | $R^2$ = 3-$NH_2$<br>$R^3$ = 5-$CONH_2$ | m.p. 176-181° C. (decomposition)<br>IR$\nu_{Max}^{KBr}$(cm$^{-1}$): 1775, 1690, 1595-1640<br>NMR ($D_2O+CF_3CO_2D$)δ:<br>2.10-2.75(2H,m), 3.35-3.60(2H,m), 3.20-3.39<br>(2H,m), 5.16(1H,t,J=9Hz), 5.25-5.81(2H,m),<br>5.35(1H,d,J=5Hz), 5.91(1H,d,J=5Hz), 7.20<br>(1H,s), 8.01-8.11(1H,m), 8.38-8.49(1H,m)<br>8.50-8.60(1H,m) |
| 26 | $R^2$ = 3-$NH_2$<br>$R^3$ = 5-Cl | m.p. 160-170° C. (decomposition)<br>IR$\nu_{Max}^{KBr}$ (cm$^{-1}$): 1770, 1690, 1610<br>NMR ($D_2O+CD_3CN$)δ:<br>2.10-2.60(2H,m), 3.20-3.50(2H,m), 3.08-3.75<br>(2H,m), 4.90(1H,t,J=9Hz), 4.80-5.50(2H,m)<br>5.13(1H,d,J=5Hz), 5.72(1H,d,J=5Hz), 6.86(1H,s),<br>7.52-7.61(1H,m), 8.18-8.25(2H,m) |
| 27 | $R^2$ = 3-$CH_2OH$<br>$R^3$ = 5-$OCH_3$ | m.p. 180-190° C. (decomposition)<br>NMR($D_2O$)δ:<br>2.1-2.7(2H,m), 3.17(1H,d,J=18Hz), 3.1-3.7(2H,m)<br>3.65(1H,d,J=18Hz), 3.97(3H,s), 4.78(2H,s),<br>4.98(1H,t,J=7Hz), 5.22(1H,d,J=5Hz), 5.23(1H,d,<br>J=14Hz), 5.52(1H,d,J=14Hz), 5.77(1H,d,J=5Hz),<br>6.83(1H,s), 7.91(1H,br,s), 8.45(1H,br.s), 8.55(1H,<br>br.s) |
| 28 | $R^2$ = 3-$CONH_2$<br>$R^3$ = 5-$OCH_3$ | m.p. 165-180° C. (decomposition)<br>NMR($D_2O+CF_3COOD$)δ:<br>2.1-2.7(2H,m), 3.15-3.90(4H,m), 4.10(3H,s),<br>5.10(1H,t,J=8Hz), 5.29(1H,d,J=5Hz), 5.35(1H,d,<br>J=15Hz), 5.75(1H,d,J=15Hz), 5.84(1H,d,J=5Hz),<br>7.10(1H,s), 8.35-9.0(3H,m) |

TABLE 1-continued

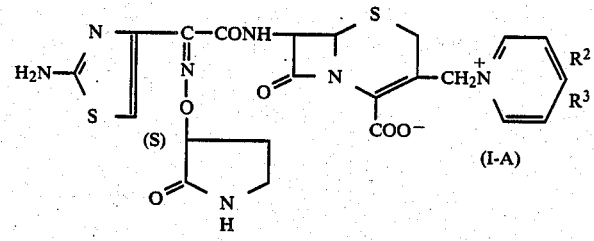

| EX No. | Compound (I-A) R² & R³ | Properties |
|---|---|---|
| 29 | R² = 3-F<br>R³ = H | m.p. 175–190° C. (decomposition)<br>NMR($D_2O$)δ:<br>2.0–2.6(2H,m), 3.2–3.8(4H,m), 4.93(1H,t,J=7Hz),<br>5.17(1H,d,J=5Hz), 5.28(1H,d,J=15Hz), 5.57(1H,<br>d,J=15Hz), 5.73(1H,d,J=5Hz), 6.89(1H,s), 7.8–<br>9.0(4H,m) |
| 30 | R² = 3-NHCOCH$_2$OH<br>R³ = H | m.p. 180–200° C. (decomposition)<br>NMR($D_2O$)δ:<br>2.1–2.7(2H,m), 3.15(1H,d,J=18Hz) 3.1–3.6(2H,m),<br>3.63(1H,d,J=18Hz), 4,22(2H,s), 4,83(1H,t,<br>J=7Hz), 5.18(1H,d,J=5Hz), 5.32(1H,d,J=7Hz), 5.54<br>(1H,d,J=7Hz), 5.74(1H,d,J=5Hz), 6.79(1H,s), 7.86<br>(1H,d,d,J=8Hz,J=6Hz), 8.38(1H,d,J=8Hz), 8.57(1H,d,<br>J=6Hz), 9.33(1H,br.s) |

Note: The compound (I-A) has (Z)—configuration.
(S) means that the carbon atom has (S)—configuration.

EXAMPLES 31 TO 60

The corresponding starting compounds are treated in the same manner as described in Example 3 or 4 to give the compounds shown in Table 2.

TABLE 2

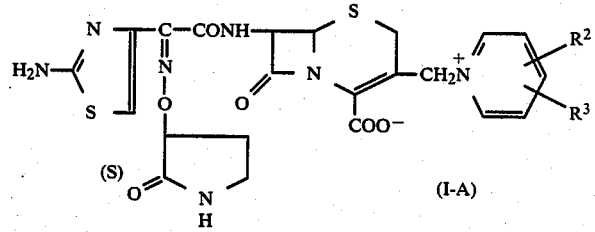

| EX No. | Compound (I-A) R² & R³ | Properties |
|---|---|---|
| 31 | R² = 4-SCH$_3$<br>R³ = H | IR$\nu_{Max}^{Nujol}$ (cm$^{-1}$): 1780<br>NMR ($D_2O$)δ:<br>2.0–2.7(2H,m), 2.49(3H,s), 3.0–3.8(4H,m), 4.89<br>(1H,t,J=7Hz), 5.00(1H,d,J=15Hz), 5.08(1H,d,J=5Hz),<br>5.43(1H,d,J=15Hz), 5.64(1H,d,J=5Hz), 6.88(1H,s),<br>7.47(2H,d,J=7Hz), 8.22(2H,d,J=7Hz) |
| 32 | R² = 4-SCH$_2$CH$_2$OH<br>R³ = H | IR$\nu_{Max}^{Nujol}$ (cm$^{-1}$): 1780, 1690, 1610<br>NMR ($D_2O$+CF$_3$CO$_2$D)δ:<br>2.0–2.5(2H,m), 2.9–3.5(6H,m), 3.68(2H,t,J=6Hz),<br>4.6–5.0(2H,m), 5.02(1H,d,J=5Hz), 5.40(1H,d,J=14Hz)<br>5.60(1H,d,J=5Hz), 6.82(1H,s), 7.48(2H,br.d,J=6Hz),<br>8.19(2H,d,J=6Hz) |
| 33 | R² = 4-SCH$_2$COOH<br>R³ = H | IR$\nu_{Max}^{Nujol}$ (cm$^{-1}$): 1770, 1690, 1610<br>NMR ($D_2O$)δ:<br>2.0–2.6(2H,m), 3.10(1H,d,J=18Hz), 3.15–3.55(2H,m),<br>3.56(1H,d,J=18Hz), 3.80(2H,s), 4.8–5.4(3H,m),<br>5.15(1H,d,J=5Hz), 5.72(1H,d,J=5Hz), 6.80(1H,s),<br>7.53(2H,d,J=5Hz), 8.36(2H,d,J=5Hz) |
| 34 | R² = 3-SO$_2$NH$_2$<br>R³ = H | IR$\nu_{Max}^{Nujol}$ (cm$^{-1}$): 1775, 1690, 1610<br>NMR ($D_2O$+CD$_3$OD+CF$_3$CO$_2$D)δ:<br>2.1–2.6(2H,m), 3.0–3.4(2H,m), 3.10(1H,d,J=17Hz),<br>3.58(1H,d,J=17Hz), 4.81(1H,t,J=8Hz), 5.02(1H,d,<br>J=5Hz), 5.16(1H,d,J=14Hz), 5.60(1H,d,J=14Hz),<br>5.61(1H,d,J=5Hz), 6.84(1H,s),8.01(1H,d,d,J=8.6Hz),<br>8.70(1H,d,J=8Hz), 8.93(1H,d,J=6Hz), 9.25(1H,s) |
| 35 | R² = 3-SO$_3$Na<br>R³ = H | IR$\nu_{Max}^{Nujol}$ (cm$^{-1}$): 1785, 1690, 1620<br>NMR ($D_2O$)δ: |

TABLE 2-continued

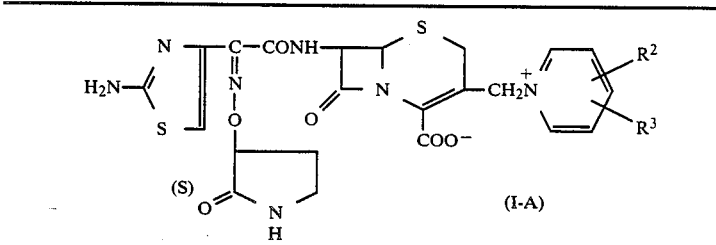

(I-A)

| EX No. | Compound (I-A) $R^2$ & $R^3$ | Properties |
|---|---|---|
| | | 2.1–2.6(2H,m), 3.07–3.75(4H,m), 4.95(1H,t,J=7Hz), 5.19(1H,d,J=5Hz), 5.30(1H,d,J=18Hz), 5.65(1H,t, J=18Hz),5.77(1H,d,J=5Hz), 6.90(1H,s),8.90(1H,d,d, J=9.6Hz), 8.71(1H,d,J=9Hz), 8.96(1H,d,J=6Hz), 9.23(1H,s) |
| 36 | $R^2$ = 4-SO$_2$CH$_3$<br>$R^3$ = H | IR$\nu_{Max}^{Nujol}$ (cm$^{-1}$): 1775, 1690, 1610<br>NMR (D$_2$O+CD$_3$OD+CF$_3$CO$_2$D)δ:<br>2.1–2.8(2H,m), 3.1–3.8(4H,m), 3.42(3H,s), 4.98(1H, t,J=8Hz), 5.2–5.8(2H,m), 5.22(1H,d,J=5Hz), 5.80 (1H,d,J=5Hz), 6.96(1H,s), 8.49(2H,d,J=6Hz), 9.31(2H,d,J=6Hz) |
| 37 | $R^2$ = 3-NHCOCH$_3$<br>$R^3$ = H | IR$\nu_{Max}^{Nujol}$ (cm$^{-1}$): 1775, 1690, 1610<br>NMR (D$_2$O)δ:<br>2.16(3H,s), 2.1–2.8(2H,m),2.9–3.8(4H,m), 4.92(1H, t,J=7Hz), 5.17(1H,d,J=5Hz), 5.2–5.8(2H,m), 5.73 (1H,d,J=5Hz), 6.73(1H,s), 7.6–7.9(1H,m), 8.0– 8.3(1H,m),8.4–8.7(1H,m), 9.27(1H,s) |
| 38 | $R^2$ = 3-NH$_2$<br>$R^3$ = H | IR$\nu_{Max}^{Nujol}$ (cm$^{-1}$): 1770, 1690, 1660<br>NMR (D$_2$O+CD$_3$OD+CF$_3$CO$_2$D)δ:<br>2.2–2.7(2H,m), 3.2–3.5(2H,m), 3.21(1H,d,J=18Hz), 3.67(1H,d,J=18Hz), 4.95(1H,t,J=7Hz), 5.11(1H,d, J=15Hz), 5.21(1H,d,J=5Hz), 5.55(1H,d,J=15Hz), 5.82(1H,d,J=5Hz), 6.95(1H,s), 7.5–7.6(2H,m), 7.9–8.2(2H,m) |
| 39 | $R^2$ = 3-NHCONH$_2$<br>$R^3$ = H | m.p. 167–200° C. (decomp.)<br>IR$\nu_{Max}^{Nujol}$ (cm$^{-1}$): 1770, 1690, 1605<br>NMR (D$_2$O+CF$_3$CO$_2$D)δ:<br>1.9–2.8(2H,m), 3.0–3.9(4H,m), 4.94(1H,t,J=8Hz), 5.0–5.9(2H,m), 5.15(1H,d,J=5Hz), 5.82(1H,d,J=5Hz), 6.94(1H,s), 7.5–8.5(3H,m), 9.10(1H,br.s) |
| 40 | $R^2$ = 4-CH$_3$<br>$R^3$ = H | NMR (D$_2$O)δ:<br>2.0–2.8(2H,m), 2.60(3H,s), 3.1–3.6(2H,m), 3.15 (1H,d,J=17Hz), 3.62(1H,d,J=17Hz), 4.92(1H,t, J=7Hz), 5.21(1H,d,J=5Hz), 5.27(1H,d,J=15Hz), 5.43(1H,d,J=15Hz), 5.76(1H,d,J=5Hz), 6.84(1H,s), 7.73(2H,d,J=6Hz), 8.60(2H,d,J=6Hz) |
| 41 | $R^2$ = 2-CH$_3$<br>$R^3$ = H | NMR (D$_2$O)δ:<br>2.1–2.7(2H,m), 2.73(3H,s), 3.1–3.6(4H,m), 4.90 (1H,t,J=7Hz), 5.11(1H,d,J=5Hz), 5.17(1H,d, J=15Hz), 5.42(1H,d,J=15Hz), 5.69(1H,d,J=5Hz), 6.78(1H,s), 7.5–7.8(2H,m), 8.0–8.3(1H,m), 8.52(1H,br d,J=6Hz) |
| 42 | $R^2$ = 3-CH$_3$<br>$R^3$ = H | NMR (D$_2$O)δ:<br>2.0–2.6(2H,m), 2.45(3H,s), 3.0–3.7(4H,m), 4.90 (1H,t,J=7Hz), 5.13(1H,d,J=5Hz), 5.15(1H,d, J=16Hz), 5.42(1H,d,J=16Hz), 5.70(1H,d,J=5Hz), 6.80(1H,s), 7.6–7.9(1H,m), 8.0–8.3(1H,m), 8.4–8.7(2H,m) |
| 43 | $R^2$ = 3-CH$_2$CH$_3$<br>$R^3$ = H | NMR (D$_2$O)δ:<br>1.27(3H,t,J=7Hz), 2.1–2.6(2H,m), 2.83(2H,q,J=7Hz), 3.1–3.6(4H,m), 4.95(1H,t,J=7Hz), 4.9–5.6(2H,m), 5.18(1H,d,J=5Hz), 5.73(1H,d,J=5Hz), 6.82(1H,s), 7.79(1H,d,d,J=8.5Hz), 8.22(1H,d,J=8Hz), 8.59 (1H,d,J=5Hz),8.63(1H,s) |
| 44 | $R^2$ = 4-CH$_2$CH$_3$<br>$R^3$ = H | NMR (D$_2$O)δ:<br>1.28(3H,t,J=8Hz), 2.1–2.6(2H,m), 2.88(2H,q,J=8Hz), 3.1–3.6(4H,m), 4.95(1H,t,J=8Hz), 4.9–5.6(2H,m), 5.18(1H,d,J=5Hz), 5.72(1H,d,J=5Hz), 6.80(1H,s), 7.70(2H,d,J=8.5Hz), 8.59(2H,d,J=8Hz) |
| 45 | $R^2$ = 2-CH$_3$<br>$R^3$ = 3-CH$_3$ | NMR (D$_2$O)δ:<br>2.1–2.8(2H,m), 2.45(3H,s), 2.68(3H,s), 3.0–3.6 (4H,m), 4.95(1H,t,J=7Hz), 5.15(1H,d,J=5Hz), 5.25 (1H,d,J=16Hz), 5.55(1H,d,J=16Hz), 5.75(1H,d, J=5Hz), 6.83(1H,s), 7.58(1H,br.d,J=7Hz), 7.08(1H, d,J=7Hz), 8.41(1H,d,J=7Hz) |
| 46 | $R^2$ = 3-CH$_3$<br>$R^3$ = 4-CH$_3$ | NMR (D$_2$O)δ:<br>2.0–2.7(2H,m), 2.38(3H,s), 2.48(3H,s), 3.0–3.7 |

TABLE 2-continued

[Structure of compound (I-A): 2-aminothiazole linked via C=N-O to a pyrrolidinone, attached to CONH-cephem nucleus with CH₂-pyridinium bearing R² and R³ substituents]

| EX No. | Compound (I-A) R² & R³ | Properties |
|---|---|---|
| | | (4H,m), 4.97(1H,t,J=7Hz), 5.1-5.5(2H,m), 5.19(1H, d,J=5Hz), 6.82(1H,s), 7.65(1H,d,J=7Hz), 8.4-8.6 (2H,m) |
| 47 | R² = 3-CH₃<br>R³ = 5-CH₃ | NMR (D₂O)δ:<br>2.1-2.6(2H,m), 2.38(6H,s), 2.9-3.7(4H,m), 4.89(1H, t,J=7Hz), 4.8-5.5(2H,m), 5.11(1H,d,J=5Hz), 5.68 (1H,d,J=5Hz), 6.72(1H,s), 7.91(1H,s), 8.33(2H,s) |
| 48 | R² + R³ = 2,3-trimethylene | NMR (D₂O)δ:<br>2.0-2.7(4H,m), 2.9-3.6(8H,m), 4.6-5.6(3H,m), 5.13 (1H,d,J=5Hz), 5.74(1H,d,J=5Hz), 6.79(1H,s), 7.56 (1H,d,J=6.5Hz), 8.04(1H,d,J=6Hz), 8.35(1H,d,J=5Hz) |
| 49 | R² = 2-SCH₂CH₃<br>R³ = H | IR$\nu_{Max}^{Nujol}$ (cm⁻¹): 1780, 1690, 1610<br>NMR (D₂O)δ:<br>1.40(3H,t,J=3Hz), 2.1-2.6(2H,m), 3.0-3.5(6H,m), 4.92(1H,d,J=7Hz), 5.08(1H,d,J=5Hz),5.13(1H,t, J=15Hz), 5.54(1H,d,J=15Hz), 5.70(1H,d,J=5Hz), 6.80(1H,s), 7.35-7.6(1H,m), 7.69(1H,d,J=7Hz), 7.95-8.2(1H,m), 8.50(1h,d,J=6Hz) |
| 50 | R² = 2-SC₂H₄NHCHO<br>R³ = H | IR$\nu_{Max}^{Nujol}$ (cm⁻¹): 1775, 1690, 1610<br>NMR (D₂O)δ:<br>2.05-2.65(2H,m),3.05-3.75(8H,m), 4.91(1H,t,J=7Hz), 5.09(1H,t,J=5Hz),5.13(1H,t,J=15Hz), 5.47(1H,d, J=15Hz), 5.70(1H,d,J=5Hz), 6.80(1H,s), 7.5-8.25 (3H,m), 7.90(1H,s), 8.55(1H,d,J=6Hz) |
| 51 | R² = 3-N(CH₃)₂<br>R³ = H | IR$\nu_{Max}^{Nujol}$ (cm⁻¹): 1775, 1690, 1610<br>NMR (D₂O+CF₃CO₂D)δ:<br>2.1-2.7(2H,m), 3.00(6H,m), 3.1-3.8(4H,m), 5.01 (1H,t,J=8Hz), 5.15(1H,t,J=18Hz), 5.23(1H,d, J=5Hz), 5.63(1H,d,J=18Hz), 5.76(1H,d,J=5Hz), 7.03(1H,s), 7.5-7.7(2H,m), 7.75-8.1(2H,m) |
| 52 | R² = 3-N(CHO)—CH₃<br>R³ = H | IR$\nu_{Max}^{Nujol}$ (cm⁻¹): 1770, 1685, 1610<br>NMR (D₂O)δ:<br>2.05-2.65(2H,m), 3.05-3.75(8H,m), 3.30(3H,s), 3.2-3.7(4H,m), 4.95(1H,t,J=8Hz), 5.20(1H,t,J=5Hz), 5.2-5.7(2H,m), 5.74(1H,d,J=5Hz), 6.85(1H,s), 7.8-9.4(5H,m) |
| 53 | R² = 3-NHCH₃<br>R³ = H | IR$\nu_{Max}^{Nujol}$ (cm⁻¹): 1770, 1685, 1620<br>NMR (D₂O+CF₃CO₂D)δ:<br>2.1-2.7(2H,m), 2.83(3H,m), 3.26(1H,t,J=18Hz), 3.3-3.6(2H,m), 3.70(1H,t,J=18Hz), 5.06(1H,d,J=8Hz), 5.15(1H,d,J=15Hz), 5.27(1H,d,J=5Hz), 5.63(1H,d, J=15Hz), 5.81(1H,d,J=5Hz), 7.08(1H,s), 7.5-7.65 (2H,m), 7.8-8.0(2H,m) |
| 54 | R² = 3-NHSO₂CH₃<br>R³ = H | IR$\nu_{Max}^{Nujol}$ (cm⁻¹): 1770, 1690, 1610, 1150<br>NMR (D₂O+CF₃CO₂D)δ:<br>2.1-2.7(2H,m), 3.24(3H,s), 3.2-3.75(4H,m), 5.03 (1H,d,J=8Hz), 5.2-5.9(2H,m), 5.26(1H,d,J=5Hz), 5.82(1H,d,J=5Hz), 7.05(1H,s), 7.8-8.85(4H,m) |
| 55 | R² = 4-NH₂<br>R³ = H | IR$\nu_{Max}^{Nujol}$ (cm⁻¹): 1775, 1690, 1610,<br>NMR (D₂O+CF₃CO₂D)δ:<br>2.1-2.6(2H,m), 3.2-3.7(4H,m), 4.95(1H,t,J=8Hz), 5.0-5.5(2H,m), 5.15(1H,d,J=5Hz), 5.70(1H,d,J=5Hz), 6.96(1H,s), 7.7-7.9(2H,m), 8.3-8.6(2H,m) |
| 56 | R² = 3-Cl<br>R³ = H | IR$\nu_{Max}^{Nujol}$ (cm⁻¹): 1775, 1690, 1610,<br>NMR (D₂O)δ:<br>2.0-2.6(2H,m), 3.1-3.5(4H,m), 4.95(1H,t,J=8Hz), 5.14(1H,d,J=16Hz), 5.74(1H,d,J=5Hz), 6.83(1H,s), 7.8-8.1(1H,m), 8.3-8.6(1H,m),8.7-8.9(1H,m), 9.04 (1H,d,J=2Hz) |
| 57 | R² = 3-CH₂NHCHO<br>R³ = H | IR$\nu_{Max}^{Nujol}$ (cm⁻¹): 1775, 1680<br>NMR (D₂O)δ:<br>2.1-2.6(2H,m), 3.1-3.6(4H,m), 4.55(2H,s), 4.90 (1H,t,J=8Hz), 5.0-5.6(2H,m), 5.15(1H,d,J=5Hz), 5.70(1H,d,J=5Hz), 6.85(1H,s), 8.50(1H,s), 7.8-8.8(4H,m) |

TABLE 2-continued

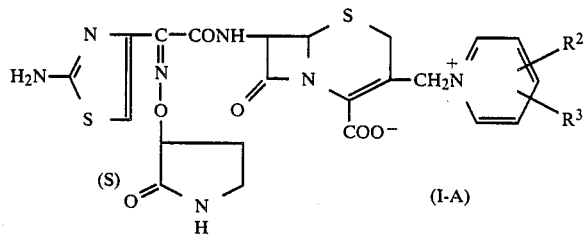

(I-A)

| EX No. | Compound (I-A) R² & R³ | Properties |
|---|---|---|
| 58 | R² = 3-CH₂NH₂<br>R³ = H | IR$\nu_{Max}^{Nujol}$ (cm⁻¹): 1770, 1685, 1610,<br>NMR (D₂O)δ:<br>2.1–2.7(2H,m), 3.18(1H,d,J=18Hz), 3.25–3.50(2H,m),<br>3.66(1H,d,J=18Hz), 4.42(2H,s), 4.96(1H,t,J=8Hz),<br>5.20(1H,d,J=5Hz), 5.32(1H,d,J=15Hz), 5.56(1H,d,<br>J=15Hz), 5.75(1H,d,J=5Hz), 6.89(1H,s), 7.9–8.2<br>(1H,m), 8.4–8.6(1H,m), 8.8–8.9(1H,m), 9.00(1H,s) |
| 59 | R² = 2-CH₂SCH₃<br>R³ = H | IR$\nu_{Max}^{Nujol}$ (cm⁻¹): 1775, 1690, 1610,<br>NMR (D₂O)δ:<br>2.20(3H,s), 2.1–2.9(2H,m), 3.1–3.8(4H,m), 4.26<br>(2H,s), 5.09(1H,t,J=7Hz), 5.32(1H,d,J=5Hz), 5.4–<br>5.85(2H,m), 5.88(1H,d,J=5Hz), 7.00(1H,s), 7.8–<br>8.1(2H,m), 8.3–8.6(1H,m), 8.7–8.9(1H,m) |
| 60 | R² = 3-OCH₃<br>R³ = H | IR$\nu_{Max}^{Nujol}$ (cm⁻¹): 1775, 1685, 1605,<br>NMR (D₂O)δ:<br>2.2–3.0(2H,m), 3.1–4.1(4H,m), 4.16(3H,s), 5.17<br>(1H,t,J=7Hz), 5.40(1H,t,J=17Hz), 5.42(1H,d,J=5Hz)<br>5.70(1H,d,J=17Hz), 5.95(1H,d,J=5Hz), 7.01(1H,s),<br>7.8–8.3(2H,m), 8.5–8.7(1H,m), 8.7–8.9(1H,m) |

[Note: The compound (I-A) has (Z)-configuration. (S) means that the carbon atom has (S)-configuration.]

EXAMPLE 61

(1) 1.65 g of (Z)-2-(2-tritylaminothiazol-4-yl)-2-[((3S)-2-oxopyrrolidin-3-yl)oxyimino]acetic acid dihydrate are dissolved in 6 ml of dimethylacetamide, and 1.84 g of phosphorus oxychloride are added dropwise thereto at −25° C. The mixture is cooled to −30° C. (The resulting solution is referred to as "Solution A".).

On the other hand, 1.43 g of p-methoxybenzyl 7β-amino-3-chloromethyl-3-cephem-4-carboxylate p-toluenesulfonate are dissolved in 6 ml of dimethylacetamide, and 2.61 g of pyridine are added thereto at −20° C. and then cooled to −30° C. The mixture is added to Solution A obtained above, and the mixture is stirred for 10 minutes. The mixture is poured into 100 ml of ice-water and insoluble materials are collected by filtration. The materials thus obtained are dissolved in ethyl acetate, washed with an aqueous sodium chloride solution, dried and then evaporated to dryness under reduced pressure. The residue is purified by silica gel chromatography (solvent, chloroform:tetrahydrofuran=2:1), and the fractions containing the desired product are collected and concentrated to dryness under reduced pressure. Ether is added to the residue, and the resulting powder is collected by filtration, whereby 1.46 g of p-methoxybenzyl 7β-{(Z)-2-(2-tritylaminothiazol-4-yl)-2-[((3S)-2-oxopyrrolidin-3-yl)oxyimino]acetamido}-3-chloromethyl-3-cephem-4-carboxylate are obtained.

m.p. 153°–155° C.

IR$\nu_{Max}^{Nujol}$ (cm⁻¹): 1790, 1700, 1605.

NMR (CDCl₃)δ: 2.20–2.60(2H, m), 3.20–3.80(4H, m), 3.73(3H, s), 4.30(1H, d, J=12 Hz), 4.56(1H, d, J=12 Hz), 4.92(1H, d, J=5 Hz), 4.96(1H, t, J=9 Hz), 5.14(2H, s), 5.81(1H, dd, J=5 Hz, J=9 Hz), 5.81(1H, dd, J=5 Hz, J=9 Hz), 6.70(1H, s), 6.80(2H, dJ=9 Hz), 7.20(15H, s), 7.25(2H, d, J=9 Hz), 8.66(1H, d, J=9 Hz).

(2) 800 mg of p-methoxybenzyl 7β-{(Z)-2-(2-tritylaminothiazol-4-yl)-2-[((3S)-2-oxopyrrolidin-3-yl)oxyimino]acetamido}-3-chloromethyl-3-cephem-4-carboxylate and 450 mg of sodium iodide are dissolved in 5 ml of acetone and the mixture is stirred at room temperature for one hour. A solution of 165 mg of 3-formylamino-2-methylpyridine dissolved in 20 ml of acetone is added to the mixture under ice-cooling, and the mixture is stirred at room temperature for 5 hours. The reaction mixture is evaporated to dryness under reduced pressure. Water is added to the residue, and the resultant solid is collected by filtration, whereby one g of p-methoxybenzyl 7β-{(Z)-2-(2-tritylaminothiazol-4-yl)-2-[((3S)-2-oxopyrrolidin-3-yl)oxyimino]acetamido}-3-[(3-formylamino-2-methyl-1-pyridinio)methyl]-3-cephem-4-carboxylate is obtained as crude product. The product thus obtained is dissolved in a mixture of 2 ml of trifluoroacetic acid and one ml of anisole, and the mixture is stirred at room temperature for 30 minutes. 20 ml of water and 20 ml of ethyl acetate are added to the mixture, and the aqueous solution is separated. The aqueous solution is adjusted to pH 5 with an aqueous sodium bicarbonate solution, and the resultant solution is passed through a column packed with CHP-20P. The column is washed with water, followed by elution with an aqueous 25% methanol solution. The fractions containing the desired product are collected and evaporated to dryness under reduced pressure. Acetone is added to the residue, and the resultant powder is collected by filtration, whereby 140 mg of 7β-{(Z)-2-(2-aminothiazol-4-yl)-2-[((3S)-2-oxopyrrolidin-3-yl)oxyimino]acetamido}-3-[(3-amino-2-methyl-1-pyridinio)-methyl]-3-cephem-4-carboxylate are obtained.

The physico-chemical properties of this product are identical with those of the product obtained in Example 6-(2).

PREPARATION OF STARTING COMPOUNDS

Preparation 1

9.5 g of sodium iodide are dissolved in 3.7 ml of water at 75° to 80° C. and 4.8 g of 3-formylamino-5-methoxypyridine and 3.8 g of 7-formylamino-cephalosporanic acid are added thereto. The mixture is stirred at 80° C. for 30 minutes. The mixture is evaporated to dryness under reduced pressure, and acetone is added to the residue. The resulting powder is collected by filtration and the powder is dissolved in 15 ml of methanol. 10 ml of 25% hydrogen chloride-methanol solution are added to the solution. The mixture is stirred at room temperature for 30 minutes and then evaporated to dryness under reduced pressure. The residue is dissolved in 10 ml of water. The solution is adjusted to pH 3.0 with 10% aqueous sodium hydroxide solution under cooling. 4.0 g of sodium iodide are added to the mixture and the mixture is stirred. The precipitated crystals are collected by filtration, washed with water and dried, whereby 2.8 g of 7β-amino-3-[(3-amino-5-methoxy-1-pyridinio)methyl]-3-cephem-4-carboxylate hydroiodide dihydrate are obtained.

m.p. 174°–179° C. (decomposition).

The following compound is obtained by treating the corresponding compound in the same manner as described above.

7β-amino-3-[(2-methylthio-1-pyridinio)methyl]-3-cephem-4-carboxylate hydroiodide.

IR$\nu_{max}^{Nujol}$ (cm$^{-1}$): 3400, 3300, 1780, 1620.

NMR (D$_2$O+CF$_3$CO$_2$D)δ: 2.80(3H, s), 3.48(2H, s), 5.16(1H, d, J=5 Hz), 5.29(1H, d, J=5 Hz), 5.45(1H, d, J=16 Hz), 5.63(1H, d, J=16 Hz), 7.57(1H, d, d, d, J=7, 6, 1 Hz), 7.78(1H, d, J=8 Hz), 8.19(1H, d, d, d, J=8, 7, 1Hz), 8.54(1H, d, d, J=6, 1 Hz)

Preparation 2

20 g of sodium iodide are dissolved in 8 ml of hot water. 8.13 g of 3-formamidopyridine and 8 g of 7-formylaminocephalosporanic acid are added to the solution, and the solution is stirred at 80° C. for 30 minutes. After cooling, 50 ml of methanol are added to the solution and then 22.2 g of concentrated hydrochloric acid are added at 15° C. The mixture is stirred at 35° C. for 30 minutes. After cooling, insoluble materials are filtered off, and the filtrate is adjusted to pH 4 with pyridine. The precipitates are collected by filtration and dried, whereby 6.14 g of 7β-amino-3-[(3-amino-1-pyridinio)methyl]-3-cephem-4-carboxylate hydroiodide are obtained.

m.p. 160°–180° C. (decomp).

IR$\nu_{Max}^{Nujol}$ (cm$^{-1}$): 3400, 3300, 3200, 1790, 1630.

NMR (D$_2$O-CF$_3$CO$_2$D)δ: B 3.40(1H, d, J=15 Hz), 3.73(1H, d, J=15 Hz), 5.20(1H, d, J=15 Hz), 5.68(1H, d, J=15 Hz), 5.2–5.4(2H, m), 7.5–7.7(2H, m), 7.9–8.2(2H, m).

What we claim is:

1. A cephalosporin compound of the formula:

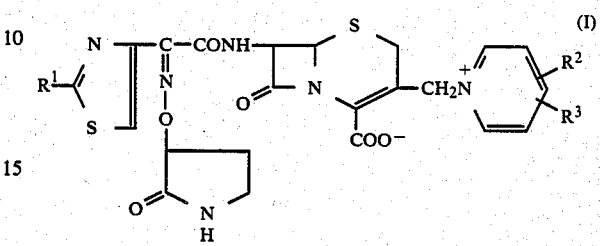

wherein R$^1$ is an amino group, either one of R$^2$ and R$^3$ is an alkyl group having one to 4 carbon atoms or an alkoxy group having one to 4 carbon atoms, and the other one of R$^2$ and R$^3$ is an amino group, or a pharmaceutically acceptable salt thereof.

2. The compound of claim 1, in which R$^1$ is an amino group, either one of R$^2$ and R$^3$ is a methoxy or methyl group, and the other one of R$^2$ and R$^3$ is an amino group.

3. The compound of claim 2 which is 7β-{(Z)-2-(2-aminothiazol-4-yl)-2-[(2-oxopyrrolidin-3-yl)oxyimino]acetamido}-3-[(3-amino-5-methoxy-1-pyridiniо)methyl]-3-cephem-4-carboxylate or a pharmaceutically acceptable salt thereof.

4. The compound of claim 3 which is 7β-{(Z)-2-(2-aminothiazol-4-yl)-2-[((3S)-2-oxopyrrolidin-3-yl)oxyimino]acetamido}-3-[(3-amino-5-methoxy-1-pyridiniо)methyl]-3-cephem-4-carboxylate or a pharmaceutically acceptable salt thereof.

5. The compound of claim 2 which is 7β-{(Z)-2-(2-aminothiazol-4-yl)-2-[(2-oxopyrrolidin-3-yl)oxyimino]-acetamido}-3-[(2-methyl-3-amino-1-pyridinio)methyl]-3-cephem-4-carboxylate or a pharmaceutically acceptable salt thereof.

6. The compound of claim 5 which is 7β-{(Z)-2-(2-aminothiazol-4-yl)-2-[((3S)-2-oxopyrrolidin-3-yl)oxyimino]-acetamido}-3-[(2-methyl-3-amino-1-pyridinio)-methyl]-3-cephem-4-carboxylate or a pharmaceutically acceptable salt thereof.

7. A pharmaceutical composition which comprises an antimicrobial effective amount of the cephalosporin compound of claim 1 or a salt thereof and a pharmaceutically acceptable carrier therefor.

* * * * *